United States Patent [19]

Anthony et al.

[11] Patent Number: 4,714,595
[45] Date of Patent: Dec. 22, 1987

[54] TISSUE STORAGE SYSTEM

[75] Inventors: Jack Anthony, Lake Bluff; Arnold C. Bilstad, Deerfield; Wayne T. Leblong, Crystal Lake; Robert J. Kruger, Arlington Heights, all of Ill.

[73] Assignee: Baxter Travenol Laboratories, Inc., Deerfield, Ill.

[21] Appl. No.: 686,948

[22] Filed: Dec. 27, 1984

[51] Int. Cl.$^4$ ............................................. B65D 81/00
[52] U.S. Cl. ................................. 422/294; 206/439; 383/103; 422/22; 422/34; 422/292
[58] Field of Search ................... 422/22, 34, 292, 294; 206/363, 439; 383/37, 103

[56] References Cited

U.S. PATENT DOCUMENTS

| | | |
|---|---|---|
| 3,123,210 | 3/1964 | Hermanson et al. . |
| 3,403,776 | 10/1968 | Denny . |
| 3,460,742 | 8/1969 | Langdon . |
| 3,468,471 | 9/1969 | Linden ................................. 422/294 |
| 3,476,506 | 11/1969 | Andersen et al. ................... 422/294 |
| 3,494,726 | 2/1970 | Barasch ............................... 422/294 |
| 3,604,616 | 9/1971 | Greif . |
| 3,685,720 | 8/1972 | Brady . |
| 3,716,961 | 2/1973 | Cope et al. ........................... 422/34 |
| 3,728,839 | 4/1973 | Glick ..................................... 422/34 |
| 3,754,700 | 8/1973 | Bonk . |
| 3,768,725 | 10/1973 | Pilaro . |
| 3,815,315 | 6/1974 | Glick ..................................... 422/34 |
| 3,819,106 | 6/1974 | Schuster . |
| 3,891,089 | 6/1975 | Goodwin et al. . |
| 3,903,335 | 9/1975 | Jones . |
| 3,926,311 | 12/1975 | Laske . |
| 4,091,921 | 5/1978 | Lewis .................................. 422/34 |
| 4,121,714 | 10/1978 | Daly et al. ........................... 422/34 |
| 4,190,154 | 2/1980 | Clark . |
| 4,194,622 | 3/1980 | Lewis .................................. 422/34 |
| 4,206,844 | 6/1980 | Thukamoto et al. . |
| 4,276,982 | 7/1981 | Sibrava et al. . |
| 4,306,656 | 12/1981 | Dahlem . |
| 4,318,506 | 3/1982 | Hirsch . |
| 4,323,189 | 4/1982 | Regenstein, Jr. . |
| 4,367,816 | 1/1983 | Wilkes . |
| 4,468,811 | 8/1984 | Shaw et al. . |

OTHER PUBLICATIONS

Films, Sheets and Laminates, a Desk Top Data Bank, Int'l Plastics Selector Inc., San Diego, CA, 1979.

Primary Examiner—Barry S. Richman
Assistant Examiner—William R. Johnson
Attorney, Agent, or Firm—Paul C. Flattery; James D. Ryndak; Bradford R. L. Price

[57] ABSTRACT

A storage system (10) includes an interior envelope (12) and an exterior envelope (14). Tissue or other material to be stored may be placed in interior envelope (12), sealed and placed in exterior envelope (14). Exterior envelope (14) is sealable in a first sealed position that allows gas sterilization of the interior of exterior envelope (14) and the contents contained therein. After sterilization, exterior envelope (14) is sealed in a gas impermeable position. Each of interior and exterior envelopes (12, 14) have one side which is transparent. A grid (22) may be provided on the transparent side of interior envelope (12) for sizing tissue contained therein.

24 Claims, 12 Drawing Figures

TISSUE STORAGE SYSTEM

FIELD OF THE INVENTION

The present invention relates to a system and method for storing material and, in particular, the storage, preservation and sterile presentation of human tissue.

BACKGROUND ART

Currently, no effective tissue storage system is available for general use. Individual clinics and hospitals devise their own methods. Often, relatively large glass jars or crocks are utilized. The use of such containers is cumbersome and tedious, especially in a sterile environment, such as an operating room. Further, such containers are subject to breakage and it is difficult to sterilize them.

It would be desirable to provide a tissue storage system that avoids the use of glass containers. Further, it would be desirable to provide a tissue storage system that would allow sterilization of the system in a closed container such as by radiation or ethylene oxide gas sterilization. It would also be advantageous to provide a tissue storage system for storage in a nonsterile environment which would include a sterile container that would be presentable in a sterile environment, such as the sterile portion of an operating room, for presentation of the tissue.

While it has been known to store specimens in a polyester pouch, a storage system has not been heretofore provided which provides the desirable characteristics as previously described.

DISCLOSURE OF THE INVENTION

In accordance with the present invention, a storage system is provided that is especially suitable for containing tissue. The storage system includes an interior or first thin film container having a sealable opening for containing tissue or other non-liquid material. This container has a transparent portion for viewing the contents contained therein and a gas permeable portion to allow gas sterilization of the interior of the first container and its contents. An exterior or second thin film container is provided that is dimensioned to contain said first container. This container also has a sealable opening and a transparent portion for viewing the contents in the first container when contained in the second container. The opening of the exterior container should be large enough to accommodate insertion of the interior container. The second container is constructed of material which provides an air and water or gas barrier for its contents when the container is sealed. The exterior container can be constructed of thin film material that has a very high degree of gas impermeability, so that tissue or other material can be stored for an extended period of time. Preferably, the exterior container is gas impermeable. As used herein, "gas impermeable" means that the container material or the container has a water vapor permeability value of about 0.05 units or less (the units being grams-mil/100 square inches/24 hours at 90% relative humidity, 37.8° C. (100° F.), using a Permatron-W instrument, manufactured by Mocon Modern Controls, Inc., Minneapolis, Minn.) and an oxygen permeability value of about 0.10 units or less (the units being cubic centimeters-mil/100 square centimeters/24 hours/atmosphere at 23° C. (73° F.), using ASTM test method D3985-81).

Preferably, the gas permeable portion of the first container will be a barrier for microorganisms. Thus, if either of the two containers is punctured, the product will remain sterile.

In accordance with a more specific embodiment of the present invention, the second or exterior container includes a gas permeable portion and is sealable in a first sealed position that allows gas sterilization of the first container and its contents through the gas permeable portion of the second container. The second container is also sealable in a second sealed position in which the second container provides a gas barrier and is preferably gas impermeable. Thus, the invention contemplates the placing of the tissue or other material in the first container, sealing the first container and placing the first container in the second container and sealing the second container in the first sealed position. The interior of the second container can then be sterilized, together with the first container and its contents. Thereafter, the second container can be sealed in the second sealed position in which the second container is gas impermeable.

The transparent portions of the first and second containers allow the contents to be viewed when stored therein and a grid may be provided as part of the first container to permit sizing of the contents contained therein. For example, the transparent portion of the first container or the second container may have the grid printed directly thereon. The materials of the containers can be chosen to allow radiation sterilization (Gamma radiation, for example) of the containers and contents stored therein.

In accordance with one embodiment of the present invention, the first and second containers each comprise an envelope or a pouch. Advantageously, the envelope or pouch may be constructed from two sheets of material that are joined together at the periphery of the sheets, each of the envelopes having a sealable opening. Other configurations may be used and are within the scope of the invention. The opening may comprise an unjoined peripheral portion of two sheets of material, or as a slit in one of the sheets, for example. The sheets of material can be any desired shape, such as rectangular, triangular or circular, for example.

In accordance with a more specific embodiment of the present invention, a storage system is provided that includes a first, flexible, sealable envelope for containing, for example, tissue, which comprises two sheets of material joined together at the periphery of the sheets with an unjoined peripheral region of the the sheets defining a sealable opening. One of the sheets is transparent for viewing tissue contained therein and the other of these sheets is gas permeable to allow gas sterilization of the interior and its contents. A second, flexible, sealable envelope is provided for containing the first envelope. The second envelope includes first and second gas impermeable sheets of material joined together at the periphery of the sheets with an unjoined peripheral region of the sheets defining a sealable opening. One of the sheets is transparent for viewing the contents contained within the first envelope. The sealable opening of the second envelope is sealable in a first sealed position which allows the interior of the second envelope to be gas sterilized. The second envelope is sealable in a second sealed position which provides gas impermeable container.

Preferably, the first gas impermeable sheet includes a portion that extends beyond the second gas impermeable sheet at the sealable opening of the second envelope and the second envelope further includes a strip of gas permeable material bonded to and overlapping the second gas impermeable sheet at the sealable opening, the strip also overlapping the first gas impermeable sheet for defining with the first sheet the first sealed position. The unjoined peripheral region of the second gas impermeable sheet defines with the first sheet the second sealed position.

The envelopes are preferably made of materials that are attachable by heat sealing. Similarly, the opening of each envelope is preferably heat sealable and may comprise an unjoined peripheral portion of two sheets which define the envelope. Preferably the containers are constructed of flexible, thin-film material.

In accordance with one embodiment, the envelopes are openable by peeling apart the joined sheets which define the envelopes. Preferably, the sheets of each envelope are joined together with at least one V-shaped or chevron shaped seal for facilitating the opening of the envelopes and the sterile presentation of the tissue.

The materials of the containers generally should be suitable for medical applications. The materials and thicknesses can be chosen to impart the desired strength, toughness, flexibility, gas permeability or impermeability, and resistance to high and low temperature. The sheets utilized in making the containers or envelopes can consist of multiple thin layers of different materials of desired thicknesses, each material chosen to provide a specific property, such as gas impermeability, strength, toughness, resistance to puncture, and flexibility and strength at low temperature. The sheets may be formed by bonding the different layers together, such as with a suitable adhesive material or by coextruding the various materials to form a sheet having layers of desired thickness.

In accordance with the invention, a method of storing material, including tissue, is provided that includes: (a) placing the material in a first sealable container or envelope as previously described; (b) sealing the material therein; (c) placing the first container in a second container or envelope as previously described which is sealable in a first sealed position which allows gas sterilization of the interior of the second container and sealable in a second sealed position in which the second container is gas impermeable; (d) sealing the second container; (e) sterilizing the interior and contents of the second container, including the first container and its contents. In one embodiment, in step (d) the second container is sealed in the first sealed position and step (e) comprises gas sterilization. In this embodiment, a further step is included which comprises sealing the second container in the second sealed position after gas sterilization, allowing storage in a gas impermeable environment. In accordance with another embodiment, in step (d) the second container is sealed in the second sealed position and step (e) comprises radiation sterilization.

It is not necessary for steps (a)–(e) to occur sequentially, although they may occur in that sequence. For example, the first container would be placed within the second container prior to sealing the first container or prior to placing material in the first container. Similarly, the sterilization of the contents of the second container would occur prior to sealing the second container, if done without breaching the sterility of the container system. Other sequences may also be feasible.

After sealing the material within the gas impermeable environment, the material may be stored for the desired period of time at the desired temperature. The storage system can be stored in a non-sterile environment and yet delivery and examination of the material or tissue within a sealed container can be made in a sterile environment without breaching the sterility of that environment. This is accomplished by removing the first sealed container from the second sealed container in the non-sterile environment and transferring the first sealed container to the sterile environment. The material can then be examined in a sterile environment without the necessity of removing the material from the first sealed container, which is sterile. The material can be removed from the first container in the sterile environment for its intended use.

In accordance with another embodiment of the invention, the first container is suitable for storing liquid. In this embodiment, the materials of the first container or envelope are selected such that they are gas impermeable. In accordance with the invention, such containers can be radiation sterilized.

BRIEF DESCRIPTION OF THE DRAWINGS

The present invention can be more completely understood by reference to the accompanying drawings in which.

DETAILED DESCRIPTION

Figure 1:
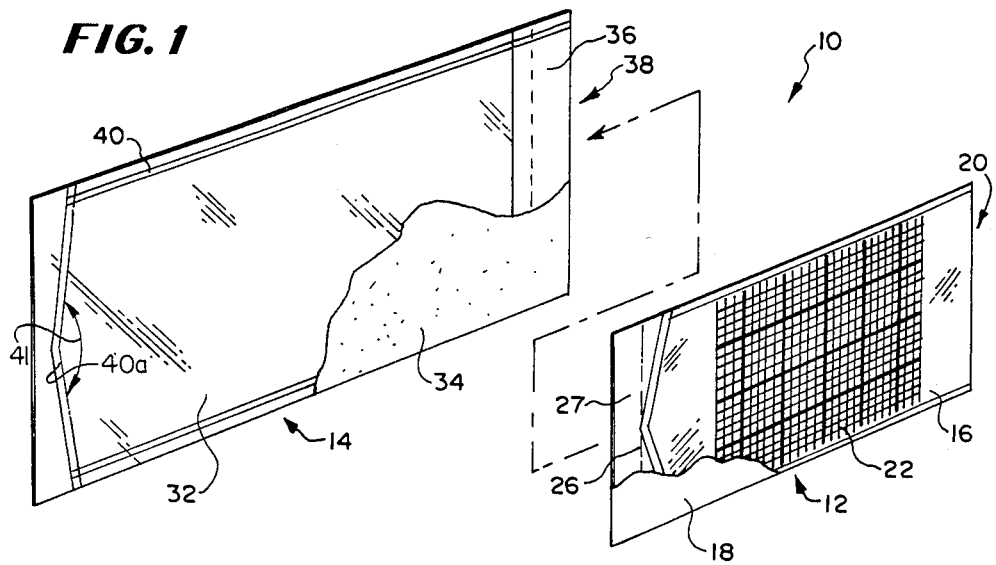
FIG. 1 illustrates a perspective front elevation view, partially cut away, of the storage system in accordance with the present invention.
Figure 2:
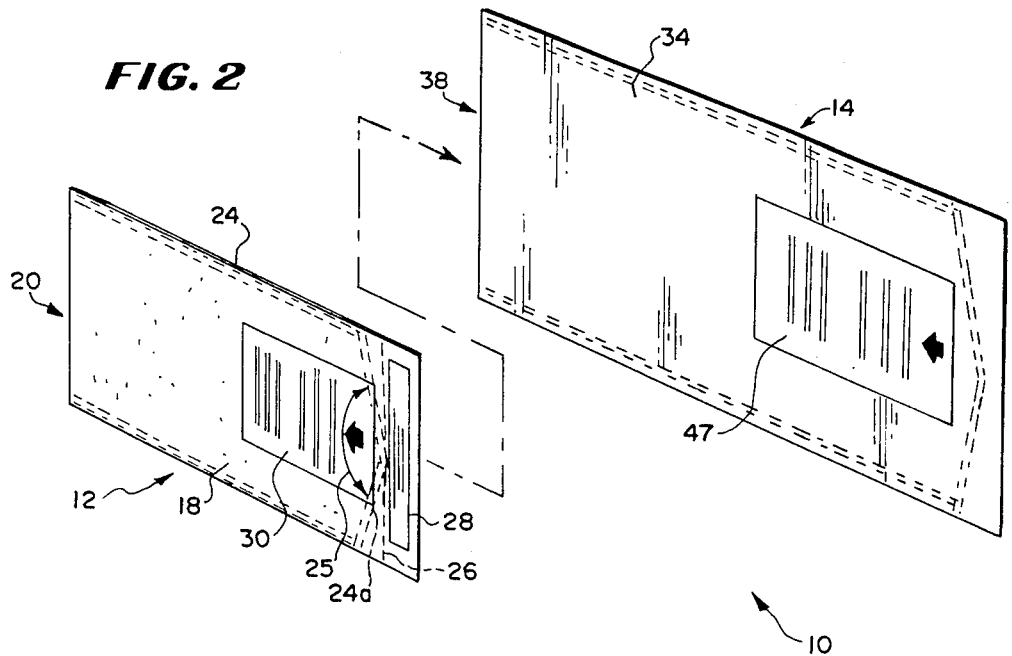
FIG. 2 illustrates a perspective rear elevation view of the storage system of FIG. 1.

Referring now to the drawings generally and in particular to FIGS. 1 and 2, there is illustrated a storage system 10 which is especially suited for storing tissue. Storage system 10 includes interior or first envelope 12 and an exterior or second envelope 14. First envelope 12 consists of two opposing rectangular sheets or webs of material 16 and 18. Sheets 16 and 18 are joined together at their periphery along three perimeter sides thereof, the unjoined fourth perimeter sides or peripheral region of sheets 16 and 18 define a sealable opening 20.

Sheet 16 is a flexible, thin film transparent sheet made up of several layers of thin film materials. Specifically, sheet 16 consists of an outer layer of nylon film having a thickness of about 0.001" and an inner layer of a heat sealable ethylene vinyl acetate modified polyethylene with an ethylene vinyl acetate content of about 4.5% to 5% and a thickness of about 0.002". These layers are bonded together with a suitable adhesive for medical uses. One especially suitable nylon film is marketed by the E.I. DuPont de Nemours Co. (DuPont) under the trademark Dartek® 66. Especially suitable ethylene vinyl acetate modified polyethylene film is available from DuPont under the trademark Elvax®. A polycarbonate resin can be used in place of the nylon and is commercially available under the trademark Lexan® of the General Electric Co. A polyester film, such as DuPont Mylar®, can also be used as a replacement for the nylon film. The nylon material is suitable for printing and is illustrated in FIG. 1, the interior side of the nylon layer of sheet 16 has printed thereon a grid 22. Grid 22 can be of the desired dimensions and as illustrated has a small grid scale of one centimeter per division and a large grid scale of five centimeters per division. If desired, the grid could be printed on the exterior of sheet 16, for example, or on second envelope 14.

Preferably, and as illustrated in FIG. 1, sheet 16 is transparent to visible light so the contents can be viewed. The materials of the containers are also capable of withstanding radiation sterilization such as gamma radiation.

Sheet 18 of envelope 12, more completely illustrated in FIG. 2, is flexible and gas permeable to allow gas sterilization of the interior of envelope 12. One suitable type of gas sterilization is ethylene oxide sterilization, which is well known in the art.

Suitable materials for sheet 18 include, for example, spun bond polymer materials, such as spun bond polyolefin, and paper. Preferably, the paper is coated with a suitable material to allow heat sealing to sheet 18. The entire surface of the paper may be coated or only the areas or zones that are intended to form a seal. Thus, the paper is preferably coated over at least a portion thereof with the heat sealing material. Suitable coating materials for heat sealing of paper include, for example, ethylene vinyl acetate, ethylene methylacrylate, ionomer resins such as Surlyn® resins and/or hot melt adhesives. One especially suitable material for sheet 18 is marketed by E.I. DuPont deNemours under the name Tyvek®, which is a spun bond polyethylene having a thickness of 0.008 inches and is a microorganism barrier. The spun bond polymer material may have a coating thereover to facilitate peeling open the container. The peelable seal provided by the coating material results in a seal of less strength than the strength of the spun bond polymer. Such materials are well known in the art. The peelable coating may be only on those portions that are intended to form a seal. Materials such as an ethylene vinyl acetate copolymer, with a vinyl acetate of 5-28% and preferably about 20%, can be used to provide a peelable seal.

Preferably, and as illustrated in FIG. 2, sheets 18 and 16 are sealed together with a seal 24 formed by application of heat to sheets 18 and 16 along the desired perimeter areas thereof. Preferably, one side of sheets 16 and 18 will be sealed together with a chevron or V-shaped seal, referred to in FIG. 2 by reference numeral 24a.

Figure 12:
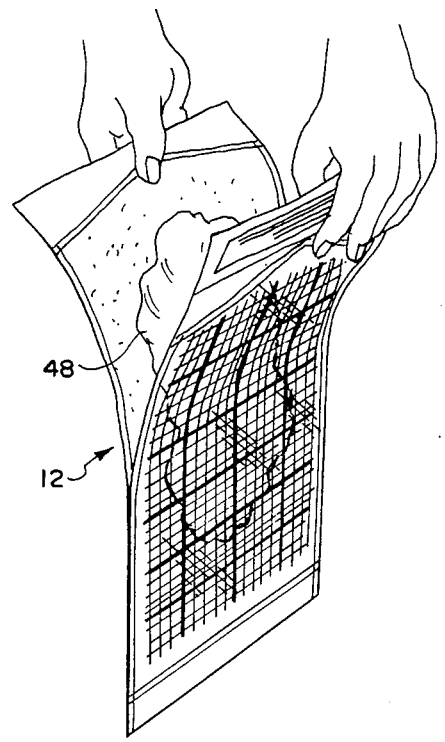
FIG. 12 illustrates in perspective view opening of the interior or first container of the storage system of FIG. 1.

The angle of V-shaped seal 24a indicated by reference numeral 25 is about 160°. V-shaped seal 24a facilitates the opening of envelope 12. When sheets 16 and 18 are peeled apart beginning with the end of envelope 12 where seal 24a is located, as shown in FIG. 12, seal 24a is gradually opened, thereby requiring less force than if seal 24a was configured as a straight line.

For the storage of liquid materials, sheets 16 and 18 of envelope 12 can be constructed of gas impermeable material, such as the previously described material of sheet 16 or other material which provides a desired barrier to liquid and gas, if desired. In this embodiment, radiation sterilization would be used. The other advantages of the storage system apply to this embodiment, which can be used to store liquid or other material, including tissue.

As illustrated in FIGS. 1 and 2, the end of first envelope 12 opposite the end where opening 20 is located includes a line of perforations 26 that extends across the width of envelope 12. The perforations allow end portion 27 to be folded over so that label 28, printed or affixed on sheet 18, is visible from the front of envelope 12. Label 28 may contain desired information or blank space for a description of the contents of envelope 12, for example. Sheet 18 may also have printed thereon another label 30, illustrated in FIG. 2, having desired information.

Figure 10:
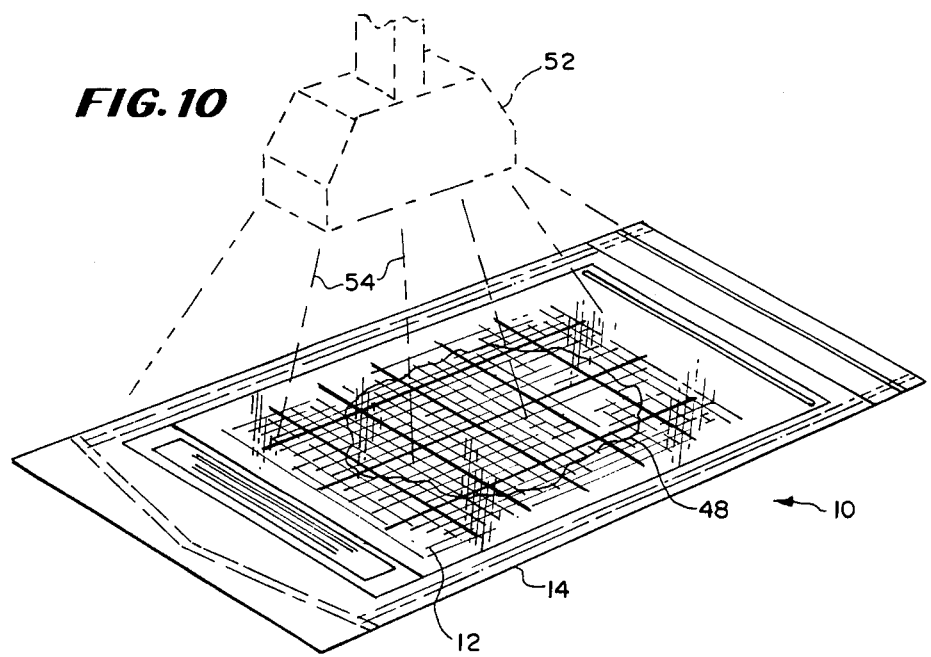
FIG. 10 illustrates radiation sterilization of the contents of the storage system of FIG. 1.

Referring to FIGS. 1 and 2, the front and rear of exterior or second envelope 14 are illustrated in perspective view. Second envelope 14 includes a first sheet 32 and a second sheet 34 which are attached together about perimeter portions thereof along three perimeter sides thereof with a seal 40, which is a heat seal. The unjoined fourth perimeter sides or peripheral region of first sheet 32 and second sheet 34, together with gas permeable strip 36, defines a sealable opening 38 of second envelope 14. Preferably, and as illustrated in FIGS. 1 and 2, seal 40 includes along one side of first and second sheets 32 and 34 a chevron or V-shaped seal 40a for facilitating opening of second envelope 14 as illustrated in FIG. 10, in a manner similar to that described with respect to first envelope 12. Angle 41 formed by V-shaped seal 40a of second envelope 14 is about 160°.

Figure 3:
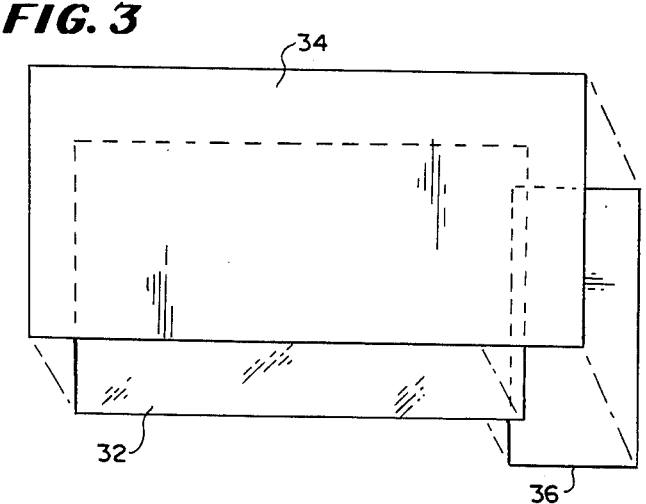
FIG. 3 illustrates a perspective exploded view of the exterior or second container of the storage system.
Figure 4:
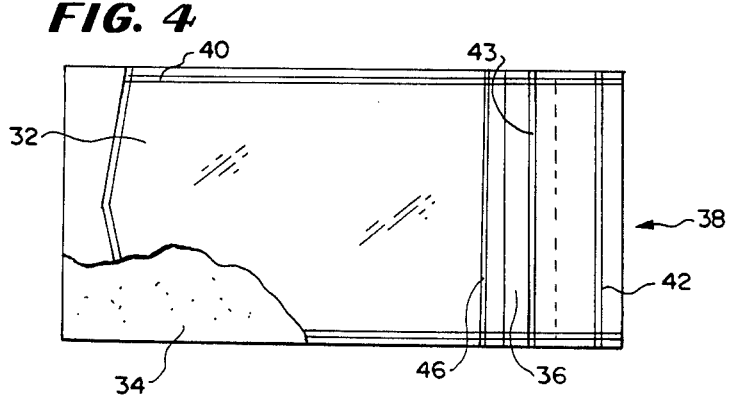
FIG. 4 illustrates a plan view, partially cut away, of the exterior or second container of the storage system.
Figure 8:
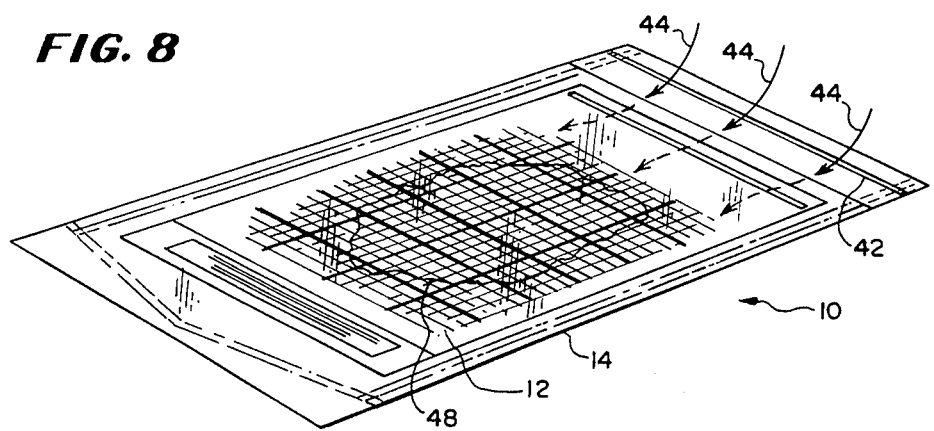
FIG. 8 illustrates in perspective view gas sterilization of the storage system of FIG. 1.

The construction of second envelope 14 is shown in greater detail in FIGS. 3 and 4. As illustrated therein, one end of sheet 34 extends beyond sheet 32. Gas permeable strip 36 overlaps and is attached to the end of sheet 32 is substantially coextensive with the portion of sheet 34 which extends beyond sheet 32. Strip 36 is attached to sheet 32 with a seal 43, which is a heat seal. Seal 40 also seals strip 36 along the sides of sheets 32 and 34 to which strip 36 is adjacent. By sealing sealable opening 38 in an area where second sheet 34 and gas permeable strip 36 overlap directly after placing contents therein, such as along line 42 of FIGS. 4 and 8, envelope 14 is sealed in a first sealed position. This allows the interior of second envelope 14 to admit sterilizing gas, such as ethylene oxide, to enter the interior of envelope 14 as illustrated in FIG. 8 by arrows 44.

When the desired gas sterilization has been completed, second envelope 14 can be sealed in the second sealed position, where first sheet 32 and second sheet 34 directly overlap, such as along line 46 of FIG. 4.

First sheet 32 and second sheet 34 of second envelope 14 are gas impermeable. First sheet 32 is a thin film, flexible, transparent sheet and is constructed in the illustrated embodiment of several layers of different material. Specifically, from outside to inside, the layers are a thin nylon film, a thin polyvinylidene chloride film and a thin film of a linear low density polyethylene material. The combination of these layers provides a clear, tough, flexible sheet 32 which is crack resistant, even at extremely low temperature such as about −80° C. Further, it forms. an excellent barrier to oxygen, water and other gases. Each of the layers of sheet 32 are bonded together using suitable adhesive material. If desired, polyester can be substituted for the nylon layer.

Specific materials which are especially suitable for making sheet 32 include a nylon film marketed by DuPont under the name Dartek ® having a thickness of about 0.001 inches, a polyvinylidene chloride (saran) marketed by Dow Chemical Company under the trade designation "XO 1621.10" having a thickness of about 0.002 inches and a linear low density polyethylene material marketed by DuPont under the name Sclair ® SL3 having a thickness of about 0.002 inches.

Suitable adhesive material for bonding the various layers of material include urethane and polyester adhesives. Several specific adhesives which may be used include available under the trademark Adkote ® 333, 548 and 575 from the Morton Chemical Co. Adkote ® 333 is believed to be a single component urethane adhesive and Adkote ® 548 and 575 are believed to be two component polyester adhesives. Other suitable adhesives will be known to those skilled in the art.

Second sheet 34 can be constructed of material similar to first sheet 32. Preferably, second sheet 34 is a laminated, flexible, thin film sheet that includes a foil layer that is sandwiched between a thin polyester layer and a linear low density polyethylene layer with the polyester layer forming the outer layer of sheet 34.

Especially suitable materials for sheet 34 include polyester material having a thickness of about 0.00048 inches marketed by DuPont, 3M Co. and ICI Americas, Inc. aluminum foil having a thickness of about 0.001 inches and a linear low density polyethylene material marketed by DuPont under the name Sclair ® SL3 having a thickness of about 0.002 inches. The layers are bonded together with suitable adhesive material.

Preferably, at least the portions of sheets 32 and 34 that are sealed together have coated at the seal interface a coating that facilitates peeling apart of the joined sheets after heat sealing. The coating results in a bond between the two sheets that is of less strength than the strength of either of the sheets. Suitable materials for forming a peelable coating on polyethylene are ethylene vinyl acetate copolymers having a vinyl acetate content of 5% to 28% and preferably about 20%. Another suitable material is available from Rollprint Packaging Products, Inc. of Addison, Il. under the trade designation RP-1A, which includes a solvent carrier. Good results have been obtained with application rates of from three to four pounds of RP-1A per 3000 square feet of sheet material. Other suitable coatings for this purpose will be known to those skilled in the art.

Second envelope 14 may have printed or affixed thereon a suitable label 47, illustrated in FIG. 2 on the reverse side of envelope 14.

Figure 5:
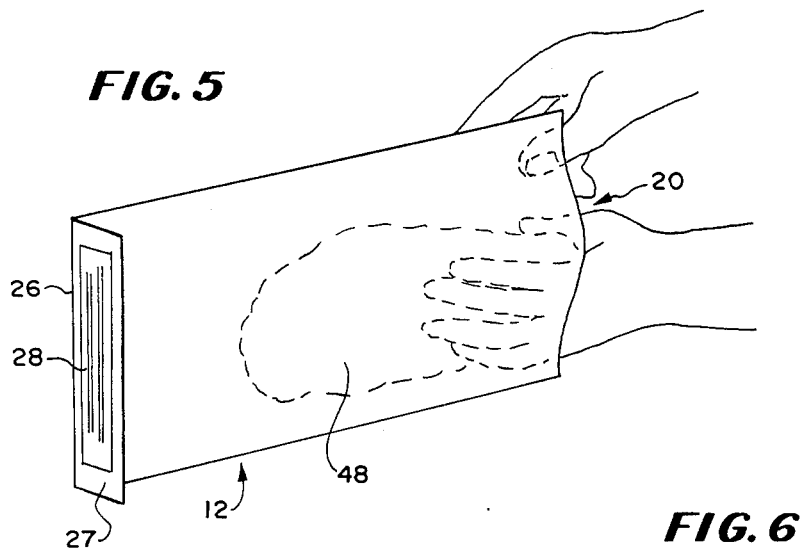
FIG. 5 illustrates in perspective view the insertion of tissue into the first or interior container of the storage system.
Figure 6:
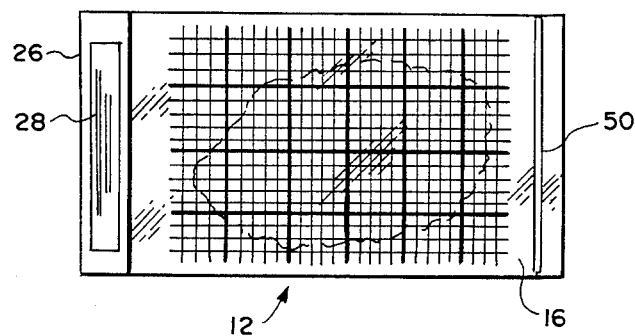
FIG. 6 illustrates a front elevation view of tissue stored within the first or interior container of the storage system.

Referring to FIG. 5, there is illustrated tissue 48 being inserted into opening 20 of interior envelope 12. After insertion of tissue 48, interior envelope 12 is sealed along seal line 50, as illustrated in FIG. 6. This may be accomplished by heat sealing, for example.

Figure 7:
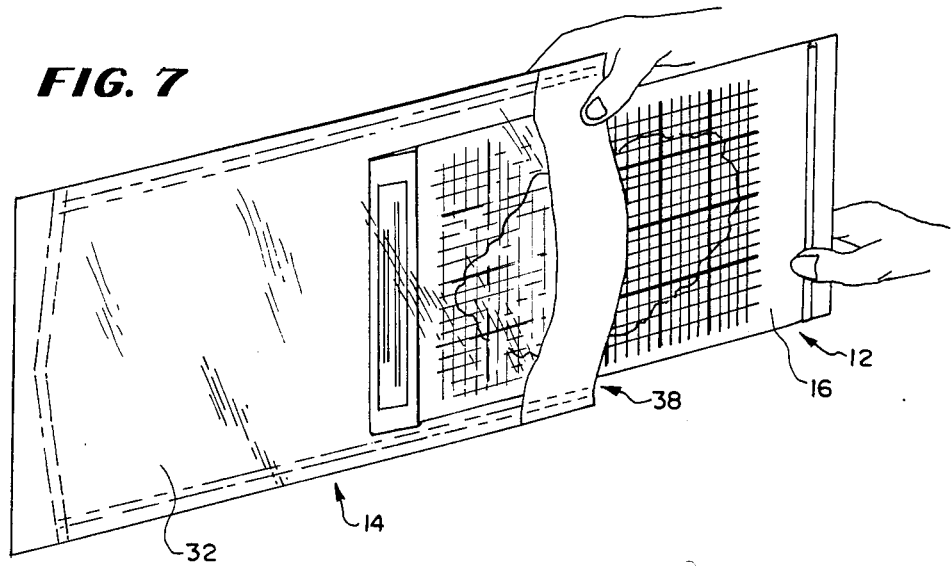
FIG. 7 illustrates in perspective view the insertion of a sealed interior or first container being inserted into the exterior or second container of the storage system.

Thereafter, as illustrated in FIG. 7, sealed interior envelope 12 is placed into exterior envelope 14 through opening 38 thereof with transparent sheets 16 and 32 in the same orientation for viewing the contents of envelope 12. Exterior envelope is then sealed along seal line 42 which allows the interior of exterior envelope 14 to be gas sterilized since a gas passageway is provided to the interior of exterior envelope 14 through gas permeable strip 36. Gas sterilization of the contents of exterior envelope 14 is illustrated in FIG. 8.

Figure 9:
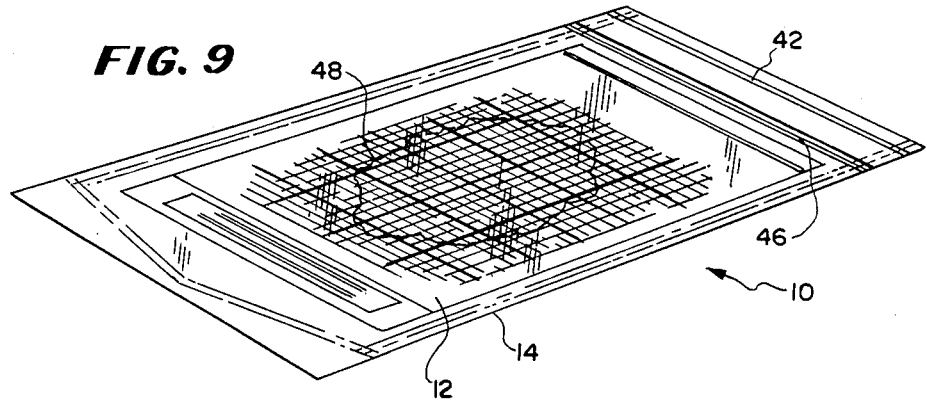
FIG. 9 illustrates in perspective the storage system of FIG. 1 after sterilization and sealing of the exterior container in the gas impermeable or second sealed position.

After gas sterilization has been completed, exterior envelope 14 is sealed in the second sealed position which is gas impermeable, along line 46 as illustrated in FIG. 9 creating a gas impermeable container.

If desired, as an alternative to gas sterilization, the interior and contents of second envelope 14 can be radiation sterilized. FIG. 10 illustrates this procedure in which a radiation source 52 directs sterilizing radiation, such as gamma radiation 54 through the transparent sheets 32 and 16 of second envelope 14 and first envelope 12, respectively.

Figure 11:
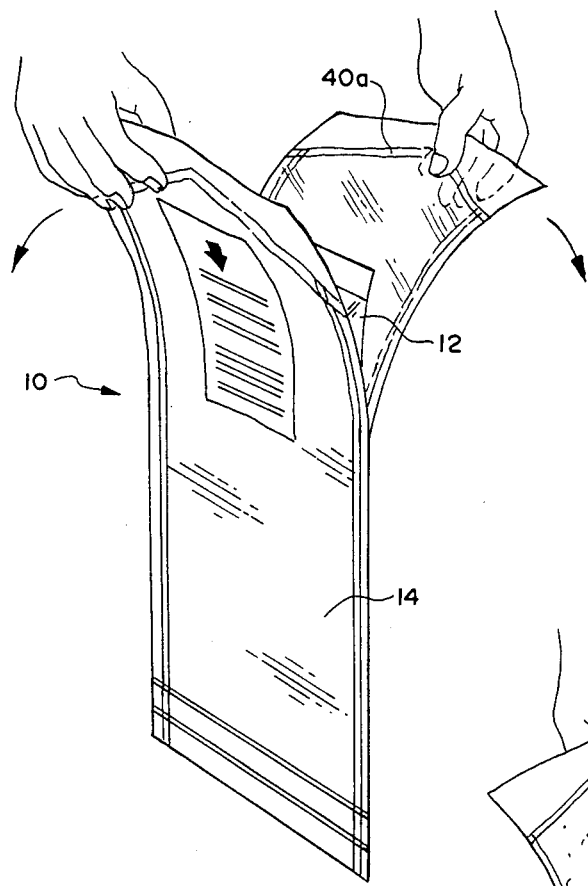
FIG. 11 illustrates in perspective view opening of the exterior or second container of the storage system of FIG. 1.

FIGS. 11 and 12 illustrate the opening of tissue storage system 10. First, exterior envelope 14 is opened by peeling apart first sheet 32 and second sheet 34. Preferably, the peeling apart is initiated along the side having V-shaped seal 40a. First sheet 32 and second sheet 34 are peeled apart sufficiently to allow interior envelope 12 to be removed therefrom. Thereafter, if desired, interior envelope 12, which has been sterilized, can be transferred to a sterile environment for opening. As illustrated in FIG. 12, interior envelope 12 is opened in the same manner as exterior envelope 14, preferably beginning with the side of interior envelope 12 that has V-shaped seal 24a. Sheets 16 and 18 are sufficiently peeled apart to allow tissue 48 to be conveniently removed therefrom.

The storage system of the present invention is particularly suited for storing human tissue. As used herein, "tissue" is used in a broad sense and includes any multicellular human or animal matter, such as skin, bone, dura matter, organs and organ parts, for example. It is to be understood that while the storage system of the invention is primarily intended for storing tissue numerous other types of material can be stored therein. By way of example only, and not as a limitation on the invention, the storage system of the present invention would be useful for storing surgical instruments and supplies, for storing industrial components and parts, for storing agricultural materials such as seeds and for storing nutritional products.

While the invention has been described with respect to preferred embodiments, it will be understood that the invention is capable of numerous changes, modifications and rearrangements and such are intended to be covered by the appended claims.

We claim:

1. A storage system comprising:

(a) a first thin film container for containing material to be sterilized, having means defining a sealable opening, means defining a transparent portion for viewing the material contained therein and a gas permeable portion to allow gas sterilization of the interior of said first container; and (b) a second thin film container, dimensioned to contain said first container, having a selectively sealable opening which includes a gas permeable portion and which is selectively sealable in a first sealed portion that allows gas sterilization of the first container through said gas permeable portion of said second container, said second container being selectively sealable in a second sealed position in which said second container provides a gas barrier, and a gas impermeable transparent portion for viewing the material in said second container providing a gas barrier when sealed.

2. The storage system of claim 1 wherein said transparent portions of said first and second containers are transparent to gamma radiation.

3. The storage system of claim 1 wherein said first and second containers each comprise an envelope.

4. The storage system of claim 1 wherein said first and second containers respectively comprise first and second envelopes, each envelope comprising two sheets of material joined together at the periphery of said sheets.

5. The storage system of claim 4 wherein each of said sealable openings comprises a peripheral portion where said two sheets are not joined together.

6. The storage system of claim 4 wherein said sheets of said first and second envelopes are joined together by heat sealing.

7. The storage system of claim 4 wherein said first and second envelopes each include a V-shaped seal for facilitating opening of said envelopes.

8. The storage system of claim 4 wherein said first and second envelopes are rectangular.

9. The storage system of claim 4 wherein one sheet of each envelope is transparent.

10. The storage system of claim 4 wherein one sheet of said second envelope is transparent.

11. The storage system of claim 10 wherein said transparent sheet of said second envelope comprises, in sequential order: p1 (a) a thin layer selected from the group consisting of nylon and polyester; p1 (b) a thin layer of polyvinylidene chloride; and p1 (c) a thin layer of linear low density polyethylene, said layers being bonded together.

12. The storage system of claim 10 wherein the other sheet of said second envelope comprises, in sequential order, a thin layer of polyester or nylon material, a thin layer of aluminum, a thin layer of linear low density polyethylene and a peelable coating over at least a portion of said polyethylene layer, said layers being bonded together.

13. The storage system of claim 4 wherein one sheet of material of said first envelope is gas permeable and the other sheet of material of said first envelope is transparent.

14. The storage system of claim 13 wherein said gas permeable sheet comprises spun bond polyolefin material.

15. The storage system of claim 13 wherein said transparent sheet material of said first envelope comprises: p1 (a) a thin layer of material selected from the group consisting of nylon, polyester and polycarbonate resin; and p1 (b) a thin layer of ethylene vinyl acetate modified polyethylene, said layers being bonded together.

16. The storage system of claim 13 wherein said gas permeable sheet comprises paper.

17. The storage system of claim 16 wherein material which allows said paper to be heat sealed to the other sheet of material of said first envelope is coated over at least the peripheral portion of said paper where the sheets are to be joined.

18. A tissue storage system comprising: p1 (a) a first flexible, sealable envelope for containing tissue, said first envelope comprising two sheets of material joined together at a portion of the periphery of said sheets, an unjoined peripheral region of said sheets defining a sealable opening, one of said sheets being transparent for viewing tissue contained therein and the other of said sheets being gas permeable to allow gas sterilization of the interior; and p1 (b) a second, flexible, sealable envelope for containing said first envelope, said second envelope comprising first and second gas impermeable sheets of material joined together at a portion of the periphery of said sheets, an unjoined peripheral region of said sheets defining a sealable opening, one of said sheets being transparent for viewing tissue contained within said first envelope, wherein the first sheet extends beyond said second sheet at the sealable opening of said second envelope, and said second sheet further comprises a strip of gas permeable material bonded to and overlapping said second sheet at the sealable opening of said second envelope, wherein said strip defines with said first sheet a first sealed position which allows the interior of said second envelope to be sterilized and wherein the unjoined peripheral region of said second sheet defines with said first sheet a second sealed position which is gas impermeable.

19. The storage system of claim 18 wherein the transparent sheet of said first envelope includes a grid for determining the size of material contained therein.

20. The storage system of claim 18 wherein the transparent sheet of said second envelope includes a grid for determining the size material contained therein.

21. The storage system of claim 18 wherein said transparent sheets are transparent to sterilizing radiation.

22. The storage system of claim 18 wherein the sheets of said first and second envelopes are rectangular.

23. The storage system of claim 18 wherein said first and second envelopes when sealed are openable by peeling apart the sheets of each envelope.

24. The storage system of claim 23 wherein the sheets of said first and second envelopes are joined together at one perimeter side in a V-shaped seal for facilitating peeling apart the sheets.

* * * * *